United States Patent
Ford et al.

(10) Patent No.: US 6,248,925 B1
(45) Date of Patent: Jun. 19, 2001

(54) SELECTIVE REDUCTIVE AMINATION OF NITRILES

(75) Inventors: Michael Edward Ford, Coopersburg; John Nelson Armor, Orefield, both of PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 09/425,678

(22) Filed: Oct. 22, 1999

(51) Int. Cl.⁷ .................................................. C07C 209/48
(52) U.S. Cl. ........................... 564/470; 564/415; 564/490
(58) Field of Search ..................... 564/415, 490, 564/470

(56) References Cited

U.S. PATENT DOCUMENTS

| | | | |
|---|---|---|---|
| 5,557,011 | 9/1996 | Witzel et al. | 564/492 |
| 5,648,545 | 7/1997 | Reif et al. | 564/470 |
| 5,847,220 | 12/1998 | Lassila | 564/493 |
| 5,869,653 | 2/1999 | Johnson | 540/531 |
| 5,894,074 | 4/1999 | Fuchs et al. | 564/490 |

FOREIGN PATENT DOCUMENTS 834244   2/1970   (CA) .

*Primary Examiner*—Samuel Barts
(74) *Attorney, Agent, or Firm*—Russell L. Brewer

(57) ABSTRACT

This invention pertains to an improvement in a process for the formation of secondary or tertiary amines by the catalytic reductive amination of a nitrile with a primary or secondary amine and, particularly to the reductive amination of $C_{8-20}$ nitrites with a secondary amine. The catalyst employed in the improved reductive amination process is one which has been promoted with a lithium salt or base, e.g., lithium chloride or lithium hydroxide.

47 Claims, No Drawings

SELECTIVE REDUCTIVE AMINATION OF NITRILES

BACKGROUND OF THE INVENTION

Processes for the production of amines by the catalytic reductive coupling of a primary or secondary amine with a nitrile are known and widely used to produce the corresponding secondary and tertiary amines. The resultant amines find utility as additives for fuels, catalytic promoters, surfactants, biocides and in numerous other applications.

An object of many of these processes is the development of a more selective process for reductive amination of nitrites to produce tertiary amines, especially fatty ($\geq$C8) nitrites, by reaction of the corresponding nitrile with a secondary amine. The preferred reaction is described in Equation 1.

However, selectivity often suffers, owing to a competing reaction pathway: a) reduction of the nitrile to the corresponding primary amine, and b) subsequent coupling of that amine with a second equivalent of nitrile to generate a secondary di(alkyl)amine. The pathway to this high molecular weight byproduct is described by Equation 2.

A problem associated with byproduct di(alkyl)amine (ADMA), particularly byproduct di(fatty alkyl)amine, is that not only is it difficult to separate from the desired (fatty alkyl)dimethylamine but the separation is inefficient and energy intensive owing to the high boiling points of the ADMAs.

Representative patents which describe the reductive coupling of nitrites with amines are as follows:

U.S. Pat. No. 5,648,545 discloses the catalytic amination of a wide variety of nitrites by reacting a nitrogen compound such as ammonia, or a primary or secondary amine with the nitrile at temperatures of from about 80 to 250° C. and a hydrogen pressure of 1 to 400 bar. The catalytic amination is carried out in the presence of hydrogen and the catalyst is comprised of a reduced copper oxide/zirconium oxide. Alkali metal carbonate is added to the catalyst prior to reaction. An exemplary nitrile included N-methylaminopropionitrile and representative amines reacted therewith included mono and dimethylamine.

Canadian Patent 834,244 discloses a process for continuously producing higher molecular weight secondary and tertiary amines by reacting higher molecular aliphatic nitrites with volatile primary or secondary amines. The fatty acid nitrites have a carbon content from 8 to 22 carbon atoms and include lauryl and stearyl nitrile and the low boiling amines include dimethylamine, diethylamine, etc. The catalyst is an alkali-modified copper-chromium catalyst with the alkylation being conducted at a temperature of 120 to 180° C. and 180 to 210 atmospheres hydrogen pressure. Salts of alkali metals used in preparing the alkali-modified catalysts included those of potassium and sodium.

U.S. Pat. No. 5,869,653 discloses a process for the hydrogenation of nitrites to produce primary amines. In the catalytic hydrogenation of aliphatic nitriles, the nitrile is contacted with hydrogen in the presence of a sponge or Raney® cobalt catalyst employing lithium hydroxide as a promoter. A wide variety of aliphatic nitriles ($C_{2-30}$) are suggested as being suited for conversion to the primary amine by reaction with hydrogen.

U.S. Pat. No. 5,847,220 discloses a process for the catalytic hydrogenation of a cyanopropionaldehyde alkyl acetal in the presence of a nickel or cobalt catalyst promoted with alkali metal hydroxide to form aminobutyraldehyde alkyl acetals, i.e., the primary amine derivative of the cyanoalkyl acetals. The background in the patent discloses a variety of processes for the hydrogenation of nitriles, but these processes generally deal with the hydrogenation of the nitrile itself, rather than a reductive alkylation by the reaction of the nitrile with a primary or secondary amine.

U.S. Pat. No. 5,557,011 discloses a process for producing diamines by reductive coupling of secondary amine with an aliphatic nitrie. In the background of the art, palladium/carbon catalysts were used as the primary reductive coupling catalyst. The improvement in the process wherein palladium was used as a catalyst resided in utilizing an oxidic support, such as a gamma alumina, silica, titania, zirconia, etc. which may be modified by inclusion of up to 15 wt % metal oxides of subgroups IB-VIIB, or Group VIII of the periodic table. Preparation of di-tert-amines from the corresponding dinitriles and secondary amines with palladium supported on an oxide (specifically, on an oxide selected from the group consisting of γ-alumina, silica, titania, or zirconia) or on that oxide treated with an alkali metal/alkaline earth oxide was shown.

U.S. Pat. No. 5,894,074 discloses a process for the preparation of tertiary amines from nitriles and secondary amines utilizing a palladium catalyst. The improvement in the process utilizing palladium as a catalyst or catalysts incorporating small amounts of calcium oxide, alumina magnesium oxide, etc., resided in the inclusion of a small amount at least one further metal selected from the group of 1B and Group VIII, as well as cerium and lanthanum on a support. Examples of the latter class of catalysts include 0.5 wt % palladium/alumina with 20% calcium oxide and 1.0 wt % palladium/alumina with 20% magnesium oxide.

BRIEF SUMMARY OF THE INVENTION

This invention pertains to an improvement in a process for the formation of secondary or tertiary amines by the catalytic reductive amination of a nitrile with a primary or secondary amine and, particularly to the reductive amination of $C_{8-20}$ nitrites with a secondary amine. The catalyst employed in the improved reductive amination process is one which has been promoted with a lithium salt or base, e.g., lithium chloride or lithium hydroxide.

There are numerous advantages associated with the improved catalytic/promoter process and these include:

an ability to achieve high production rates;

an ability to aminate a wide range of nitriles;

an ability to effect conversion of the nitrile group to the secondary or tertiary amine in high selectivity; and an ability to use the catalyst over an extended time.

DETAILED DESCRIPTION OF THE INVENTION

A wide variety of nitrites may be used in the reductive amination process, and these nitrites include $C_{2-30}$ aliphatic and aromatic nitrites. Specific examples of nitriles include aliphatic nitriles such as acetonitrile, propionitrile, butyronitrile and valeronitrile; ether nitriles such as ethoxypropionitrile, methoxypropionitrile, isopropoxynitrile, biscyanoethylether, bis-(2-cyanoethyl) ethyleneglycol, bis-(2-cyanoethyl)diethyleneglycol, mono-(2-cyanoethyl)diethyleneglycol, bis(2-cyanoethyl) tetramethylene glycol; fatty nitrites, preferably $C_{8-20}$ fatty alkyl nitrites, saturated and unsaturated, e.g., lauronitrile, cocoalkyl nitrile, oleonitrile, tall oil fatty acid nitrile and stearonitrile; dinitriles such as adiponitrile, methylglutaronitrile and succinonitrile; cyclic nitriles such as isophoronenitrile; α-aminonitriles such as aminoacetonitrile, imino-bis-acetonitrile and nitrilotriacetonitrile, β-aminonitriles formed by the reaction of acrylonitrile with $C_{1-30}$ alkylamines and $C_{1-8}$ alkanolamines such as β-aminopropionitrile, di-(2-cyanoethyl)amine, N-methyl-β-aminopropionitrile, N,N-dimethyl-β-aminopropionitrile, N-(2-cyanoethyl) ethanolamine, N,N-di-(2-cyanoethyl)ethanolamine, N-(2-cyanoethyl)diethanolamine and N-(2-cyanoethyl) propanolamine; β-cyanoethylated ureas, amides and lactams. Ureas suited for use are represented by the formula $R_2NCONR_2$ where R=H, $C_1$–$C_8$ alkyl radical or $CH_2CH_2CN$, e.g., N-cyanoethyl urea; cyanoethylated amides are represented by the formula; RCON $(CH_2CH_2CN)_n$ where R is H or a $C_{1-8}$ alkyl radical and n is 1 or 2 such as cyanoethylated acetamide and cyanoethylated propionamide and the cyanoethylated lactams are represented by the formula: $(CH_2)_m CONCH_2CH_2CN$ where m is 3, 4 or 5. N-cyanoethyl caprolactam is an example.

Representative aromatic nitrites which may be used in the process include: benzyl cyanide, benzonitrile, isophthalonitrile and terephthalonitrile. However, the preferred class of nitrites are the fatty nitrites having from 8–18 carbon atoms.

A wide variety of amines may be used in the reductive amination process. Representative amines which can be used in the reductive amination process are represented by the formula $R^1R^2NH$ where Rcan be hydrogen or lower alkyl having from ($C_1$ to $C_6$) carbons or aryl and $R^2$ can be lower aliphatic or lower alkyl having from $C_1$–$C_6$ carbons and aryl. Examples of candidate amines include primary and secondary amines such as monomethylamine, monoethylamine, monopropylamine, dimethylamine, diethylamine, dipropylamine; diamines such as ethylenediamine, propylenediamine, N,N diethylethylenediamine, N,N-dimethylethylenediamine, N,N-dimethyl-1,3-propanediamine, alkanolamines such as, ethanolamine, diethanolamine, dipropanolamine, ether amines such as methoxypropylamine, methoxyethylamine, ethoxyethylamine, diethoxyethylamine, aryl amines such as N-methylaniline, diphenylamine, and cycloaliphatic amines such as N-ethylpiperazine, cyclohexylamine and dicyclohexylamine. Preferred amines are the secondary $C_{1-4}$ alkylamines, specifically dimethylamine and diethylamine.

Palladium is the catalytic metal of choice for the reductive amination reaction. Typically, the reductive amination catalyst is carried upon a heterogeneous support for ease of removal from the reaction medium. Representative supports include carbon, alumina, silica, kielsulghur, and the like. The heterogeneous catalytic metal component, palladium, is carried on the support in an amount usually ranging from about 2 to 20% by weight and preferably from 3–10% and most preferably from 4 to 6% by weight. Other metals such as ruthenium, rhodium and platinum offer little in the way of enhanced selectivity and reaction rate.

The loading of heterogenous catalyst and particularly the palladium catalyst, including support, in the process is that loading level commonly used in prior art processes, e.g., from 0.5 wt % to 5.0 wt %, dry weight basis, based upon the nitrile feed. Preferred levels range from 1 wt % to 3 wt % palladium, dry weight basis, with respect to the nitrile feed.

The mole ratio of amine to nitrile (N/R) employed in the process must be at least stoichiometric and preferably is from 1.2 to 4.0. Although the literature teaches that a wide mole ratio range of amine to nitrile, e.g., from 1 to 30:1 may be used, levels much closer to stoichiometric, e.g., 1.2 to 2 N/R are preferred.

A key to effectiveness of the reductive amination process lies in the use of an alkali metal selected from the group consisting of sodium and lithium. (For purposes of general discussion, reference will made to lithium and such reference is intended to include sodium.) To enhance selectivity and to minimize dialkyl amine formation, lithium is added to the reaction medium in an amount of about 0.1 to 100 mmole/g of palladium catalyst (based upon palladium metal and support). Preferably, the lithium salt or base is added to the reaction medium to provide a level of from 0.4 to 25 mmole/g of catalyst and more preferably 0.4 to 2 mmole/g of catalyst.

Alkali metal compounds that may be used in the reaction medium are alkali metal hydroxides and inorganic salts. Examples include lithium hydroxide, lithium hydroxide monohydrate, lithium chloride, lithium bromide and sodium chloride. Salts of organic acids such as lithium acetate do not show enhanced selectivity.

In carrying out the reductive amination of the nitrile, it is preferred to use a medium in which the nitrile and amine are soluble but one in which the lithium salt is not. Preferably the medium is selected such that it has an affinity for hydrogen such that the hydrogen can become solubilized therein. A class of polar solvents which are particularly suited for use in the reductive amination process are the lower $C_1$–$C_6$ alkanols and particularly methanol, isopropanol, butanol, and so forth. Tetrahydrofuran and a variety of ethers such as diethyl ether may be used. Typically, the solvent is added in a proportion of about 50 to 1000%, preferably 75 to 200% by weight of the nitrile to be added to the reaction medium. Amounts larger than 200% simply expand and exacerbate the recovery problem. Of the solvents, isopropanol is a preferred solvents as it is economic and also enhances the dissolution of hydrogen therein to maintain catalyst activity during the reductive amination process.

Catalyst pretreatment with alkali metal may be effected so long as the reactant nitrile is used in conjunction with the alcohol, e.g., isopropanol.

Alkali metal salts preferably are not added at a level above about 2 millimoles per gram of heterogeneous catalyst. Two reasons are given: (1) conversion tends to diminish for a given reaction time and (2) higher levels of added salt may present a problem with respect to contamination of the reaction product. If large levels are employed, they remain with the reaction product and generally must be separated therefrom. Preferably a level from about 0.4 to 0.7 millimoles alkali metal compound is added per mol of catalyst.

The reduction of the nitrile to the amine is carried out under a hydrogen pressure of from 50 to 2000 psig, typically from 400 to 600 psig, and at temperatures of from about 100 to 180° C., typically 140 to 160° C. Typical batch reaction times range from 15 to 600 minutes.

The following examples are intended to illustrate various embodiments of the invention and are not intended to restrict the scope thereof.

COMPARATIVE EXAMPLE 1

Reductive Coupling Of Cocoalkyl Nitrile With Dimethylamine No Added Lithium Salt A 300 mL 316SS autoclave was charged with 0.625 gm (dry weight basis) of 5% palladium on carbon (Pd/C)

followed by a solution of 49.0 gm (0.25 mole) of cocoalkyl nitrile in 45.0 gm (0.75 mole) of isopropanol. The autoclave was closed, purged with nitrogen and hydrogen, charged with 13.5 gm (0.30 mole) dimethylamine, and pressurized to ca 200 psig with hydrogen. The mixture was heated with stirring at 1500 rpm to 150° C. and pressurized with hydrogen to 450 psig. The reaction was maintained at this temperature; pressure was maintained at 450 psig via regulated hydrogen feed. After 3.5 hr, the mixture was cooled to room temperature, and the product removed from the reactor by filtration through an internal $0.5\mu$ sintered metal element. Analysis of the product was done by GC and GC-MS.

EXAMPLE 2

Reductive Coupling Of Cocoalkyl Nitrile With Dimethylamine Promoted With Lithium Hydroxide Monohydrate The procedure of Example 1 was repeated, with addition of 0.0107 gm ($2.55 \times 10^{-4}$ mole) of lithium hydroxide monohydrate in 1.0 mL of water to the reactor after the addition of the solution of cocoalkyl nitrile in isopropanol. After 3.0 hr, hydrogen uptake appeared to be complete. The reaction was cooled to room temperature, and the product isolated and analyzed as before.

EXAMPLE 3

Reductive Coupling Of Cocoalkyl Nitrile With Dimethylamine Promoted With Lithium Hydroxide Monohydrate The procedure of Example 1 was repeated, with addition of 0.0270 gm ($6.43 \times 10^{-4}$ mole) of lithium hydroxide monohydrate in 1.0 mL of water to the reactor after the addition of the solution of cocoalkyl nitrile in isopropanol. Hydrogen uptake was noticeably slower than in Example 1. After 3.0 hr, the reaction was cooled to room temperature, and the product isolated and analyzed as before.

EXAMPLE 4

Reductive Coupling Of Cocoalkyl Nitrile With Dimethylamine Promoted With Lithium Hydroxide Monohydrate The procedure of Example 1 was repeated, with addition of 0.0190 gm ($4.53 \times 10^{-4}$ mole) of lithium hydroxide monohydrate in 1.0 mL of water to the reactor after the addition of the solution of cocoalkyl nitrile in isopropanol. Rapid hydrogen uptake was observed; it was complete within 3 hrs. After 3.0 hr, the reaction was cooled to room temperature, and the product isolated and analyzed as before.

COMPARATIVE EXAMPLE 5

Reductive Coupling Of Cocoalkyl Nitrile With Dimethylamine Promoted With Sodium Hydroxide The procedure of Example 1 was repeated, with addition of 0.018 gm ($4.50 \times 10^{-4}$ mole) of sodium hydroxide in 1.0 mL of water to the reactor after the addition of the solution of cocoalkyl nitrile in isopropanol. Slow hydrogen uptake was observed; incomplete conversion of cocoalkyl nitrile was obtained after 3 hrs. at reaction temperature.

COMPARATIVE EXAMPLE 6

Reductive Coupling Of Cocoalkyl Nitrile With Dimethylamine Promoted With Potassium Hydroxide The procedure of Example 1 was repeated, with addition of 0.0254 gm ($4.53 \times 10^{-4}$ mole) of potassium hydroxide in 1.0 mL of water to the reactor after the addition of the solution of cocoalkyl nitrile in isopropanol. Extremely slow hydrogen uptake was observed; by this measure, conversion of cocoalkyl nitrile was ca 10% after 3 hrs. at reaction temperature.

EXAMPLE 7

Reductive Coupling Of Cocoalkyl Nitrile With Dimethylamine Promoted With Lithium Acetate Dihydrate The procedure of Example 1 was repeated, with addition of 0.0808 gm ($7.94 \times 10^{-4}$ mole) of lithium acetate dihydrate (1.75 equivalents, based on lithium hydroxide monohydrate) in 1.0 mL of water to the reactor after the addition of the solution of cocoalkyl nitrile in isopropanol. Rapid hydrogen uptake was observed; it was complete after 4 hrs. The reaction was cooled to room temperature, and the product isolated and analyzed as before.

COMPARATIVE EXAMPLE 8

Reductive Coupling Of Stearonitrile With Dimethylamine No Added Lithium Salt

The procedure of Example 1 was repeated, with substitution of 66.2 gm of stearonitrile in place of the cocoalkyl nitrile previously used, and use of 0.78 gm (dry weight basis) of 5% Pd/C (to maintain the ratio of 1 wt % catalyst, dry weight basis, relative to fatty nitrile and DMA). The reaction mixture was heated with stirring at 1500 rpm to 150° C. and pressurized with hydrogen to 500 psig. Rapid hydrogen uptake was observed; it was complete within 2 hrs. After 2.0 hr, the reaction was cooled to room temperature, and the product isolated and analyzed as before.

EXAMPLE 9

Reductive Coupling Of Stearonitrile With Dimethylamine Promoted With Lithium Hydroxide Monohydrate The procedure of Example 8 was repeated, with addition of 0.0240 gm ($5.71 \times 10^{-4}$ mole) of lithium hydroxide monohydrate in 1.0 mL of water to the reactor after the addition of the solution of stearonitrile in isopropanol. Rapid hydrogen uptake was observed; it was complete within 3 hrs. After 3.0 hr, the reaction was cooled to room temperature, and the product isolated and analyzed as before.

EXAMPLE 10

Reductive Coupling Of Stearonitrile With Dimethylamine Promoted With Lithium Chloride The procedure of Example 8 was repeated, with addition of 0.0420 gm ($9.9 \times 10^{-4}$ mole) of lithium chloride in 1.0 mL of water to the reactor after the addition of the solution of stearonitrile in isopropanol. Rapid hydrogen uptake was observed; it was complete within 4 hrs. After 4.0 hr, the reaction was cooled to room temperature, and the product isolated and analyzed as before.

COMPARATIVE EXAMPLE 11

Reductive Coupling Of Stearonitrile With Dimethylamine Promoted With Sodium Chloride The procedure of Example 10 was repeated, with addition of 0.0427 gm ($1.0 \times 10^{-3}$ mole) of sodium chloride in 1.0 mL of water to the reactor after the addition of the solution of stearonitrile in isopropanol. Rapid hydrogen uptake was observed; it was complete within 4 hrs. After 4.0 hr, the reaction was cooled to room temperature, and the product isolated and analyzed as before.

was cooled to room temperature, and the product isolated and analyzed as before. The product consisted of 77% lauryldimethylamine, 20% laurylamine, 3% cocoalkyl nitrile, and a trace of di(cocoalkyl)amine.

Table 1 sets forth conditions and results.

TABLE 1

Reductive Coupling of Fatty Nitriles with Dimethylamine

| | Nitrile Feed | | | mm alk | | | Conv | Selectivity[f] | | |
|---|---|---|---|---|---|---|---|---|---|---|
| Ex | (gms) | N/R[a] | Alkali Compound | gcat[b] | T[c] | p[d] | (%)[e] | ADMA[g] | RNH$_2$[h] | (R)$_2$NH[i] |
| 1 | Cocoalkyl nitrile | 1.2 | None | 0 | 150 | 450 | 94 | 72 | 19 | 9 |
| 2 | Cocoalkyl nitrile | 1.2 | Lithium hydroxide | 0.408 | 150 | 450 | 94 | 78 | 15 | 7 |
| 3 | Cocoalkyl nitrile | 1.2 | Lithium hydroxide | 1.029 | 150 | 450 | 86 | 79 | 19 | 2 |
| 4 | Cocoalkyl nitrile | 1.2 | Lithium hydroxide | 0.725 | 150 | 450 | >99 | 93 | 4 | 2 |
| 5 | Cocoalkyl nitrile | 1.2 | Sodium hydroxide[i] | 0.720 | 150 | 450 | 90 | 71 | 23 | 6 |
| 6 | Cocoalkyl nitrile | 1.2 | Potassium hydroxide[j] | 0.725 | 150 | 450 | 10 | ND[(i)] | ND | ND |
| 7 | Cocoalkyl nitrile | 1.2 | Lithium acetate dihydrate[l] | 1.27 | 150 | 450 | 93 | 70 | 19 | 11 |
| 8 | Stearonitrile | 1.2 | None | 0 | 150 | 500 | 99 | 78 | 2 | 20 |
| 9 | Stearonitrile | 1.2 | Lithium hydroxide | 0.914 | 150 | 500 | 99 | 77 | 18 | 5 |
| 10 | Stearonitrile | 1.2 | Lithium chloride | 1.584 | 150 | 500 | >99 | 96 | 3 | trace |
| 11 | Stearonitrile | 1.2 | Sodium chloride[m] | 1.6 | 150 | 500 | >99 | 88 | 7 | 4 |
| 12 | Lauronitrile | 1.2 | None | 0 | 150 | 500 | 97 | 77 | 15 | 8 |
| 13 | Lauronitrile | 1.2 | Lithium hydroxide | 0.670 | 150 | 500 | 97 | 79 | 21 | <1 |

Notes to Table 1
[a]N/R refers to moles amine per mole of nitrile.
[b]m alk/g refers to moles alkali metal per gram catalyst.
[c]Temperature in ° C.
[d]Pressure in psig.
[e]Based on nitrile feed.
[f]Weight percent of each component in the product, on a feedstock-free basis.
[g]Alkyldimethylamine.
[h]Primary alkylamine derived from the fatty nitrile.
[i]Secondary alkylamine derived from the fatty nitrile.
[j]Equimolar quantity relative to lithium hydroxide used in run 4.
[k]Not determined.
[l]1.75 equivalents, relative to lithium hydroxide used in run 4.
[m]Equimolar quantity relative to lithium chloride used in run 9.

COMPARATIVE EXAMPLE 12

Reductive Coupling Of Lauronitrile With Dimethylamine No Added Lithium Salt

The procedure of Example 1 was repeated, with substitution of 45.0 gm of lauronitrile in place of the cocoalkyl nitrile previously used, and use of 0.585 gm (dry weight basis) of 5% Pd/C (to maintain the ratio of 1 wt % catalyst, dry weight basis, relative to fatty nitrile and DMA). The reaction mixture was heated with stirring at 1500 rpm to 150° C. and pressurized with hydrogen to 500 psig. Rapid hydrogen uptake was observed; it was essentially complete within 3 hrs. After 3.0 hr, the reaction was cooled to room temperature, and the product isolated and analyzed as before.

EXAMPLE 13

Reductive Coupling Of Lauronitrile With Dimethylamine Promoted With Lithium Hydroxide Monohydrate The procedure of Example 12 was repeated, with addition of 0.0176 gm (4.19×10$^{-4}$ mole) of lithium hydroxide monohydrate in 1.0 mL of water to the reactor after the addition of the solution of lauronitrile in isopropanol. Hydrogen uptake was complete within 5 hrs. After 5.5 hr, the reaction

COMPARATIVE EXAMPLE 14

Reductive Coupling Of Cocoalkyl Nitrile With Dimethylamine Lithium Added To Water/Pd Catalyst Dispersion A mixture of 0.62 gm (dry weight basis) of 5% Pd/C with a solution of 0.0190 gm (4.53×10$^{-4}$ mole) of lithium hydroxide monohydrate in 1.0 mL of water was prepared, and allowed to stand at room temperature for 5 minutes. Subsequently, a 300 mL 316SS autoclave was charged with the Pd/C—lithium hydroxide mixture, followed by a solution of 49.0 gm (0.25 mole) of cocoalkyl nitrile in 45.0 gm (0.75 mole) of isopropanol. The autoclave was closed, purged with nitrogen and hydrogen, charged with 13.5 gm (0.30 mole) dimethylamine, and pressurized to ca 200 psig with hydrogen. The mixture was heated with stirring at 1500 rpm to 150° C. and pressurized with hydrogen to 450 psig. The reaction was maintained at this temperature; pressure was maintained at 450 psig via regulated hydrogen feed. After 3.5 hr, the mixture was cooled to room temperature, and the product removed from the reactor by filtration through an internal 0.5μ sintered metal element. Analysis of the product was done by GC and GC-MS. Conversion of the starting cocoalkyl nitrile was 99%; selectivity (feedstock-free basis) was: 49% ADMA; 39% primary amine; and 12% di(fatty alkyl)amine.

COMPARATIVE EXAMPLE 15

Reductive Coupling Of Cocoalkyl Nitrile With Dimethylamine Lithium Added To Ru Catalyst The procedure of Example 1 was followed except that ruthenium on carbon was employed as the catalyst. No significant difference was observed between these results and those obtained with a lithium hydroxide-modified catalyzed reaction that was done under the conditions described in Example 4.

COMPARATIVE EXAMPLE 16

Reductive Coupling Of Cocoalkyl Nitrile With Dimethylamine Lithium Added To Rh Catalyst)

The procedure of Example 1 was followed except that rhodium on carbon was employed as the catalyst. No significant difference was observed between these results and those obtained with a lithium hydroxide-modified rhodium catalyzed reaction that was done under the conditions described in Example 4.

COMPARATIVE EXAMPLE 17

Reductive Coupling Of Cocoalkyl Nitrile With Dimethylamine Lithium Added To Pt Catalyst The procedure of Example 1 was followed except that platinum on carbon was employed as the catalyst. No significant difference was observed between these results and those obtained with a lithium hydroxide-modified platinum catalyzed reaction that was done under the conditions described in Example 4.

COMPARATIVE EXAMPLE 18

Reductive Coupling Of Cocoalkyl Nitrile With Dimethylamine Lithium Added To Isopropanol/Pd Catalyst Dispersion Catalyst Pretreatment. Reductive Coupling of Cocoalkyl Nitrile with Dimethylamine (0.51 wt % added lithium, based on dry weight of catalyst, as lithium hydroxide monohydrate); catalyst pretreated with lithium hydroxideIisopropanol. The run was similar to Example 14 except for the substitution of isopropanol for water.

A 300 mL 316SS autoclave was charged with 0.62 gm (dry weight basis) of 5% Pd/C, followed by 45.0 gm (0.75 mole) of isopropanol and a solution of 0.0190 gm (4.53× $10^{-4}$ mole) of lithium hydroxide monohydrate in 1.0 mL of deionized water. The reactor was blanketed with nitrogen, stirred at 1500 rpm for 0.5 hr, and then the liquid was removed by filtration through an internal $0.5\mu$ sintered metal element. (The contents of the reactor were maintained under 10 psig of nitrogen.) Subsequently, a solution of 49.0 gm (0.25 mole) of cocoalkyl nitrile in 45.0 gm (0.75 mole) of isopropanol, followed by 13.5 gm (0.30 mole) dimethylamine, were introduced into the reactor. The reactor was pressurized to ca 200 psig with hydrogen. The mixture was heated with stirring at 1500 rpm to 150° C. and pressurized with hydrogen to 450 psig. The reaction was maintained at this temperature; pressure was maintained at 450 psig via regulated hydrogen feed. Hydrogen uptake appeared to be complete after ca 4.0 hr. After 5.0 hr, the mixture was cooled to room temperature, and the product removed from the reactor by filtration through an internal $0.5\mu$ sintered metal element. Analysis of the product was done by GC and GC-MS. Conversion of the starting cocoalkyl nitrile was 98%; selectivity (feedstock-free basis) was: 66% ADMA; 28% primary amine; and 6% di(fatty alkyl)amine.

COMPARATIVE EXAMPLE 19

Reductive Coupling Of Cocoalkyl Nitrile With Dimethylamine Lithium Added To Pd Catalyst Catalyst Pretreatment. Reductive Coupling of Cocoalkyl Nitrile with Dimethylamine (0.51 wt % added lithium, based on dry weight of catalyst, as lithium hydroxide monohydrate); catalyst pretreated with lithium hydroxide/ isopropanol—cocoalkyl nitrile solution.

The procedure of the Example 18 was followed, with the difference that a solution of 49.0 gm (0.25 mole) of cocoalkyl nitrile in 45.0 gm (0.75 mole) in isopropanol was used for pretreatment of the Pd/C with the lithium hydroxide solution. Hydrogen uptake appeared to be complete after ca 4.0 hr. After 5.0 hr, the mixture was cooled to room temperature, and the product removed from the reactor by filtration through an internal 0.5 $\mu$ sintered metal element. Analysis of the product was done by GC and GC-MS. Conversion of the starting cocoalkyl nitrile was 98%; selectivity (feedstock-free basis) was: 90% ADMA; 4% primary amine; and 6% di(fatty alkyl)amine.

COMMENTS ON EXAMPLES 1–7

Examples 1–4 help to define the preferred loading of lithium as lithium salt relative to the palladium/carbon catalyst necessary to improve selectivity to the tertiary amine, cocoalkyldimethylamine, and minimize selectivity to byproduct di(cocoalkyl)amine. Note, conversion is high in all lithium promoted runs. Comparison of Examples 1 and 2 shows no significant difference between rates or product distributions. Thus, ~0.4 mmole lithium (as lithium hydroxide monohydrate) per gm of palladium/carbon (dry weight basis) appears to be too low of a loading to be effective. In contrast, while ~1.0 mmole lithium (as lithium hydroxide monohydrate) per gm of catalyst effectively blocks formation of di(cocoalkyl)amine, the reaction rate is relatively slow and conversion is diminished (see Example 3). It would appear that a 1 mm/gram level of lithium compound may be at about the upper end of the desired range in terms of reaction rate and conversion, but is more effective in achieving selectivity to ADMA. There is only a few percent of $RNH_2$ and an even smaller percentage of $R_2NH$.

Comparison of Examples 5 and 6 with Example 4 shows the selectivity differences between lithium and that of sodium and potassium. Sodium was effective in reducing the level of $R_2NH$ vis-a-vis Example 1 wherein no promoter alkali metal was used but selectivity to ADMA was poorer than was achieved with the corresponding lithium compound. Potassium hydroxide was even more of detriment to the overall reaction and evaluation reveals that potassium was ineffective as a promoter. Thus. substitution of equimolar amounts of either sodium hydroxide or potassium hydroxide results in no improvement of selectivity as well as dramatically lowering catalyst activity as compared to a corresponding level of lithium.

Comparison of Example 7 with Example 3 and 10 further shows the necessity for use of lithium hydroxide as reaction promoter. Replacement of lithium hydroxide with a significantly larger quantity (1.75 equivalents) of lithium acetate does not affect the selectivity of the palladium/carbon catalyst.

COMMENTS ON EXAMPLES 8–11

These examples show the effect of two lithium-containing catalyst modifiers on reductive amination of stearonitrile with dimethylamine.

Examples 8 and 9 show the effect of added lithium hydroxide: Conversion and selectivity to stearyldimethylamine are not affected, but selectivity to di(stearyl)amine is significantly diminished in favor of stearylamine.

Example 10 shows that formation of di(stearyl)amine can essentially be prevented by modification of the reaction medium with lithium chloride instead of lithium hydroxide. The latter permits the formation of some di(stearyl)amine, but significantly less di(stearyl)amine is formed than in a similar run in which no lithium was present.

Comparison of Examples 8, 11, and 12 shows the preference for the use of lithium chloride as a modifier to obtain the latter result. Lower selectivity to the tertiary amine, stearyldimethylamine, and higher selectivities to stearylamine and di(stearyl)amine coproducts are obtained upon replacement of lithium chloride with an equimolar quantity of sodium chloride. Lastly, the results also show that the chloride salts of both lithium and sodium are effective at the higher molar levels in terms of achieving excellent conversions and, at the same time, achieving higher selectivity to ADMA.

COMMENTS ON EXAMPLES 12–13

These examples show the effect of lithium hydroxide on reductive amination of lauronitrile with dimethylamine. Although addition of lithium hydroxide essentially prevents formation of di(lauryl)amine, conversion and selectivity to the tertiary amine, lauryidimethylamine, is not adversely effected.

COMMENTS ON COMPARATIVE EXAMPLE 15–17

Generally, lithium hydroxide-modified ruthenium, platinum and rhodium metals were not as effective as lithium hydroxide-modified palladium.

COMMENTS ON CATALYST PRETREATMENT EXAMPLES 14, 18–19

Comparison of the results obtained from the comparative Examples 17 and 18 above with the results of runs 1 and 4 (original table) shows clearly that pretreatment of the catalyst with lithium hydroxide in isopropanol is ineffective and does not enhance the selectivity to ADMAs. In contrast, the same comparison shows that pretreatment of the catalyst with lithium hydroxide in the less polar mixture of cocoalkyl nitrile and isopropanol is very effective in enhancing the selectivity to ADMA, and provides a result that is very similar to that obtained via in situ modification. These examples show that while the palladium catalyst can be effectively premodified, a relatively nonpolar solvent such as a mixture of fatty nitrile and isopropanol (or possibly a higher alcohol than isopropanol) must be used.

What is claimed is:

1. In a process for the catalytic reductive amination of nitrites which comprises reacting a nitrile with a primary or secondary amine in the presence of a heterogeneous reductive amination catalyst under hydrogen pressure and under conditions for effecting conversion of the nitrile group to the corresponding secondary or tertiary amine, the improvement in the reductive amination process for enhancing selectivity and minimizing di organo amine formation which resides in effecting the reductive amination in the presence of a promotionally effective amount of an alkaline compound selected from the group consisting of lithium compounds and sodium chloride.

2. The process of claim 1 wherein the alkaline compound is a lithium compound that is present in an amount of from 0.1 to 100 millimoles per gram of heterogeneous metal catalyst.

3. The process of claim 2 wherein the heterogeneous metal catalyst is palladium and the level of lithium compound is from 0.4 to 25 millimoles lithium compound per gram of palladium catalyst.

4. The process of claim 3 wherein the lithium compound is selected from the group consisting of lithium hydroxide, lithium hydroxide hydrate, lithium chloride, lithium carbonate, lithium bicarbonate, and lithium sulfate.

5. The process of claim 4 wherein the amine that is reacted with the nitrile is represented by the formula $R^1R^2NH$ where $R^1$ can be hydrogen or lower aliphatic having from 1–6 carbon atoms or aryl and $R^2$ can be lower aliphatic or lower alkyl having from 1–6 carbon atoms and aryl.

6. The process of claim 5 wherein the nitrile is an aliphatic nitrile having from 2–30 carbon atoms.

7. The process of claim 6 wherein the amine is a lower $C_{1-4}$ alkyl amine.

8. The process of claim 7 wherein the nitrile is a fatty nitrile is selected from the group consisting of lauronitrile, stearonitrile, cocoalkyl nitrile oleonitrile, and tallow fatty acid nitrile.

9. The process of claim 8 wherein the lithium compound is present from an amount of 0.4 to 2 millimoles per gram of palladium catalyst.

10. The process of claim 9 wherein the $C_{1-4}$ alkyl amine is a secondary amine.

11. The process of claim 10 wherein the secondary amine is dimethyl amine.

12. The process of claim 11 wherein the lithium compound is lithium hydroxide or lithium hydroxide monohydrate.

13. The process of process 12 wherein the reaction is carried out in the presence of a solvent selected from the group consisting of methanol and isopropanol.

14. The process of claim 6 wherein the aliphatic nitrile is a β-aminonitrile or a β-alkoxynitrile.

15. The process of claim 14 wherein the amine reacted with the nitrile is a lower $C_{1-4}$ alkyl amine.

16. The process of claim 8 wherein the lithium compound is present from an amount of 0.4 to 25 millimoles per gram of palladium catalyst.

17. The process of claim 16 wherein the $C_{1-4}$ alkyl amine is a secondary amine.

18. The process of claim 17 wherein the secondary amine is dimethyl amine.

19. The process of claim 18 wherein the lithium compound is lithium hydroxide or lithium hydroxide monohydrate.

20. The process of process 19 wherein the reaction is carried out in the presence of a solvent selected from the group consisting of methanol and isopropanol.

21. The process of claim 7 wherein the nitrile is a β-aminonitrile selected from the group consisting of: β-aminopropionitrile, di-(2-cyanoethyl)amine, N-methyl-β-aminopropionitrile, N,N-dimethyl-β-aminopropionitrile, N-ethyl-β-aminopropionitrile, N,N-diethyl-β-aminopropionitrile, mono-(2-cyanoethyl)methylamine; di-(2-cyanoethyl)methylamine, N-(2-cyanoethyl)ethanolamine, N,N-di-(2-cyanoethyl)ethanolamine, N-(2-cyanoethyl)diethanolamine, N-(2-cyanoethyl)propanolamine, N-(2-cyanoethyl)stearylamine, N-(2-cyanoethyl)cocoalkyamine, N-(2-cyanoethyl)oleylamine, or N-(2-cyanoethyl)cocoalkylamine.

22. The process of claim 21 wherein the amine is a lower $C_{1-4}$ alkyl amine.

23. The process of claim 22 wherein the lithium compound is present from an amount of 0.4 to 25 millimoles per gram of palladium catalyst.

24. The process of claim 23 wherein the $C_{1-4}$ alkyl amine is a secondary amine.

25. The process of claim 24 wherein the secondary amine is dimethyl amine.

26. The process of claim 23 wherein the lithium compound is lithium hydroxide or lithium hydroxide monohydrate.

27. The process of claim 5 wherein the aliphatic nitrile is an alkoxy nitrile represented by the formula:

$$R-O(-CR'HCR'H-O)_n-CH_2CH_2CN$$

where $R=C_1$ to $C_{30}$ alkyl radical, $R'=H$ or $C_1$ to $C_8$ alkyl radical and $n=1$ to 30.

28. The process of claim 12 wherein the alkoxy nitrile is selected from the mono-(2-cyanoethyl)ethylene glycol; bis-(2-cyanoethyl)ethyleneglycol, mono-(2-cyanoethyl)diethyleneglycol; bis-(2-cyanoethyl)diethyleneglycol; bis(2-cyanoethyl)tetramethyleneglycol, cyanoethyl stearyl ether, cyanoethyl oleyl ether, cyanoethyl cocoalkyl ether, or cyanoethyl lauryl ether.

29. The process of claim 28 wherein the amine is a lower $C_{1-4}$ alkyl amine.

30. The process of claim 27 wherein the lithium compound is present from an amount of 0.4 to 25 millimoles per gram of palladium catalyst.

31. The process of claim 30 wherein the $C_{1-4}$ alkyl amine is a secondary amine.

32. The process of claim 31 wherein the secondary amine is dimethyl amine.

33. The process of claim 32 wherein the lithium compound is lithium hydroxide or lithium hydroxide monohydrate.

34. The process of claim 6 wherein the nitrile is a $C_{7-15}$ aromatic nitrile.

35. The process of claim 34 wherein the aromatic nitrile is selected from the group consisting of isophthalonitrile, terephthalonitrile, benzonitrile and benzyl cyanide.

36. The process of claim 35 wherein the amine is a lower $C_{1-4}$ alkyl amine.

37. The process of claim 36 wherein the lithium compound is present from an amount of 0.4 to 2 millimoles per gram of palladium catalyst.

38. The process of claim 37 wherein the $C_{1-4}$ alkyl amine is a secondary amine.

39. The process of claim 38 wherein the secondary amine is dimethyl amine.

40. The process of claim 39 wherein the lithium compound is lithium hydroxide or lithium hydroxide monohydrate.

41. The process of claim 5 wherein the nitrile is a cyanoethylated amide represented by the formula; $RCON(CH_2CH_2CN)_n$ where R is H or a $C_{1-8}$ alkyl radical and n is 1 or 2.

42. The process of claim 41 wherein the cyanoethylated amide is selected from the group consisting of cyanoethylated acetamide and cyanoethylated propionamide.

43. The process of claim 42 wherein the amine is a lower $C_{1-4}$ alkyl amine.

44. The process of claim 43 wherein the lithium compound is present from an amount of 0.4 to 25 millimoles per gram of palladium catalyst.

45. The process of claim 44 wherein the $C_{1-4}$ alkyl amine is a secondary amine.

46. The process of claim 45 wherein the secondary amine is dimethyl amine.

47. The process of claim 45 wherein the lithium compound is lithium hydroxide or lithium hydroxide monohydrate.

* * * * *

UNITED STATES PATENT AND TRADEMARK OFFICE
CERTIFICATE OF CORRECTION

PATENT NO. : 6,248,925 B1
DATED : June 19, 2001
INVENTOR(S) : Michael Edward Ford and John Nelson Armor It is certified that error appears in the above-identified patent and that said Letters Patent is hereby corrected as shown below:

<u>Column 12,</u>
Line 19, insert a comma -- , -- after the words "cocoalkyl nitrile".

<u>Column 13,</u>
Line 16, insert the words, -- group consisting of methoxypropionitrile, bis-cyanoethylether, -- after the words "selected from the".

Signed and Sealed this

Fifteenth Day of October, 2002

*Attest:*

JAMES E. ROGAN
*Attesting Officer*           *Director of the United States Patent and Trademark Office*